United States Patent [19]

Sakamoto et al.

[11] Patent Number: 5,322,960
[45] Date of Patent: Jun. 21, 1994

[54] METHOD FOR INHIBITING POLYMERIZATION OF (METH) ACRYLIC ACID AND ESTERS THEREOF

[75] Inventors: Kazuhiko Sakamoto; Takahiro Takeda; Masatoshi Ueoka; Yoji Akazawa; Masao Baba, all of Himeji, Japan

[73] Assignee: Nippon Shokubai Co., Ltd., Osaka, Japan

[21] Appl. No.: 99,318

[22] Filed: Jul. 30, 1993

[30] Foreign Application Priority Data

Apr. 15, 1993 [JP] Japan .................................. 5-088908

[51] Int. Cl.⁵ ............................................. C07C 69/52
[52] U.S. Cl. .................................................... 560/205
[58] Field of Search .......................................... 560/205

[56] References Cited

U.S. PATENT DOCUMENTS 4,127,603 11/1978 Bljumberg et al. .

FOREIGN PATENT DOCUMENTS 1052847A 7/1991 China .
58-46496 10/1983 Japan .
1127127 9/1968 United Kingdom .

*Primary Examiner*—Paul J. Killos
*Attorney, Agent, or Firm*—Oblon, Spivak, McClelland, Maier & Neustadt

[57] ABSTRACT

Disclosed herein is a method for inhibiting polymerizable (meth)acrylic acid and esters thereof from polymerizing during their production and storage by using as the inhibitor N-oxyl compound, phenol compound, and phenothiazine compound in combination with one another. The combined use of the three inhibitors provides superior inhibiting effect to use alone alone or in pairs.

7 Claims, No Drawings

METHOD FOR INHIBITING POLYMERIZATION OF (METH) ACRYLIC ACID AND ESTERS THEREOF

BACKGROUND OF THE INVENTION

1. Field of the Invention

The present invention relates to a method for inhibiting the polymerization of (meth)acrylic acid monomers and (meth)acrylate monomers (referred to as (meth)acrylic acid and esters thereof hereinafter) that will otherwise take place during their production.

2. Description of the Prior Art

It is well-known that (meth)acrylic acid and esters thereof have a strong tendency to spontaneous polymerization by light or heat. Hence, it is common practice to add one inhibitor or more in combination to inhibit polymerization during their storage.

An example of the inhibitors which have so far been tried is N-oxyl compounds, such as di-tert-butyl nitroxide and 2,2,6,6-tetramethyl-4-hydroxypiperidinooxyl(2,2,6,6-tetramethyl-4-hydroxypiperidine-1-oxyl), as disclosed in British Patent No. 1,127,127. According to the disclosure, they are more effective than known inhibitors such as hydroquinone, phenothiazine, and cupric chloride, when they are used alone. The N-oxyl compound is also used as an inhibitor in the production of methacrylic acid from methacrolein by the aid of an oxygen-containing gas in an organic solvent. It includes 2,2,6,6-tetramethyl-4-hydroxypiperidinooxyl and 2,2,6,6-tetramethylpiperidinooxyl as disclosed in U.S. Pat. No. 4,127,603. It also includes 2,2,5,5-tetramethyl-3-oxopyrrolidinooxyl and 2,2,6,6-tetramethyl-4-acetoxypiperidinooxyl as disclosed in Japanese Patent Publication No. 46496/1983. In addition, it is shown in Chinese Patent No. 1,052,847A that 2,2,6,6-tetramethyl-4-hydroxypiperidinooxyl effectively inhibits the polymerization of acrylic acid and acrylate when used alone or in combination with hydroquinone and that this (or those) inhibitor(s) is (are) more effective than copper dibutyldithiocarbamate and hydroquinone used in combination.

Contrary to the foregoing, the present inventors found that the N-oxyl compound used alone or in combination with hydroquinone does not work satisfactorily under specific conditions. In other words, the above-mentioned inhibitor used in an ordinary amount does not work in the production of (meth)acrylic acid by catalytic gas phase reaction, because polymerization of (meth)acrylic acid easily occurs while it is separated by azeotropic distillation from its aqueous solution containing acetic acid and aldehydes. Thus, there was a problem of the formation of popcorn polymers and sticky polymers in the distillation column during distillation, which prevents the continuous operation of the plant for a long period of time. Since large amount of inhibitor was required to obtain effective inhibition, they didn't adapt for practical use.

SUMMARY OF THE INVENTION

It is an object of the present invention to provide a method for inhibiting the polymerization of (meth)acrylic acid and esters with a small amount of inhibitor thereof in the above-mentioned process.

The gist of the present invention resides in a method for inhibiting the polymerization of (meth)acrylic acid and esters thereof, said method comprising using as the inhibitor N-oxyl compound, phenol compound, and phenothiazine compound in combination with one another. According to the most desirable embodiment of the present invention, the N-oxyl compound is one or more than one kinds selected from 2,2,6,6-tetramethylpiperidinooxyl, 4-hydroxy-2,2,6,6-tetramethylpiperidinooxyl, and 4,4',4''-tris(2,2,6,6-tetramethylpiperidinooxyl)phosphite, the phenol compound is hydroquinone and/or methoquinone and the phenothiazine compound is phenothiazine.

DESCRIPTION OF THE PREFERRED EMBODIMENTS

The essential prerequisite of the present invention resides in using as the inhibitor N-oxyl compound, phenol compound, and phenothiazine compound in combination with one another. The present inventors have found that only when used together do these compounds provide a remarkable synergistic effect for inhibiting the polymerization of (meth)acrylic acid and esters thereof which they incompletely provide when used alone or in pairs. The present invention is based on this finding.

There are no specific restrictions on the N-oxyl compound used in the present invention. Its preferred examples include 2,2,6,6-tetramethylpiperidinooxyl, 4-hydroxy-2,2,6,6-tetramethylpiperidinooxyl, and 4,4',4''-tris-(2,2,6,6-tetramethylpiperidinooxyl)phosphite. They may be used alone or in combination with one another. The use of 2,2,6,6-tetramethylpiperidinooxyl or 4-hydroxy-2,2,6,6-tetramethylpiperidinooxy is desirable because they do not have metal ions. Thus, the plant device is free from corrosion and waste treatment becomes easy.

The phenol compound used in the present invention includes, for example, hydroquinone, methoquinone, pyrogallol, catechol, and resorcin. Hydroquinone and methoquinone are desirable. They may be used alone or in combination with one another.

The phenothiazine compound used in the present invention includes, for example, phenothiazine, bis-(α-methylbenzyl)phenothiazine, 3,7-dioctylphenothiazine, and bis-(α-dimethylbenzyl)phenothiazine. Phenothiazine is desirable. They may be used alone or in combination with one another.

According to the present invention, the above-mentioned three compounds, N-oxyle compound, phenol compound, and phenothiazine compound, produce a pronounced inhibiting effect while they are used in combination with one another. If necessary, they may also be used in combination with molecular oxygen to enhance the inhibiting effect and to provide the continuous operation of the plant for a long period of time.

The inhibiting method of the present invention may be favorably applied to (meth)acrylic acid and esters thereof which are particularly liable to polymerize among vinyl compounds. Examples of the acrylic ester include methyl acrylate, ethyl acrylate, butyl acrylate, 2-ethylhexyl acrylate, 2-hydroxyethyl acrylate, and 2-hydroxypropyl acrylate. Examples of the methacrylic ester include methyl methacrylate, butyl methacrylate, 2-hydroxyethyl methacrylate, and 2-hydroxypropyl methacrylate.

According to the inhibiting method of the present invention, the three inhibitors are added to (meth)acrylic acid in distillation all processes, such as rectification column, separation column from solvent, separation column from low-boiling fractions such as acetic acid, and stripper of low-boiling acrolein and methacrolein, in the case where (meth)acrylic acid is produced by the catalytic gas phase reaction.

The method of the present invention consists in adding the three inhibitors during the above-mentioned processes. The inhibitors may be added in the form of solid or powder or in the form of aqueous solution or solvent solution. The three inhibitors may be added all at once (in the form of solution) or one after another. If the inhibitor is to be added during the distillation process in the production of (meth)acrylic acid, it may be dissolved in the feed or reflux.

The amount of the three inhibitors to be used is not specifically limited, depending on the operating conditions. Usually, it is 10–1000 ppm (by weight) of the amount of evaporated monomer (or (meth)acrylic acid and esters thereof). The preferred amount of the individual inhibitors of the amount of evaporated monomer is as follows:

N-oxyl compound: 1–100 ppm
Phenol compound: 3–500 ppm
Phenothiazine compound: 3–500 ppm
(The second and third inhibitors should preferably be used in the same amount.)

The amount of evaporated monomer means the total amount of monomer vapor which is boiled up from column bottom in proportion to the amount of heat fed to the reboiler. It is an important factor to determine the amount of the inhibitors to be added.

The optional molecular oxygen may be added to (meth)acrylic acid and esters thereof directly by bubbling or indirectly by dissolution in solvents. Bubbling may be easily accomplished by introducing oxygen gas to the distillation column or stripper from their bottom and/or from the reboiler. The amount of molecular oxygen should preferably be 0.1–1.0 vol % of the amount of evaporated monomer.

The method for inhibiting polymerization of the present invention may also be effectively applied to (meth)acrylic acid and esters thereof during their transportation and storage.

The method for inhibiting polymerization of the present invention has been described above. It consists of using the three inhibitors—N-oxyl compound, phenol compound, and phenothiazine compound. The combined use of the three inhibitors provides superior inhibiting effect to use alone or in pairs. It has now become possible to prevent (meth)acrylic acid and esters thereof from polymerizing even under the condition that occurs their polymerization very easily. Thus the method of the present invention provides the uninterrupted operation of the plant for a long period and stable transportation and storage of (meth)acrylic acid and esters thereof.

EXAMPLES

To further illustrate the invention, and not by way of limitation, the following examples are given. (Unit ppm in the following examples and comparative examples is based by weight)

Example 1

Pure acrylic acid was prepared from commercial one distillation to remove inhibitors. 2 ml each of the pure acrylic acid (placed in a test tube) was incorporated with inhibitors in different amounts as shown in Table 1. (Experiments Nos. 1–6 are for comparison.) The test tube was kept reducing pressure and immersed in an oil bath at 100° C.

Induction period of polymerzation was measured by visual inspection. The results are shown in Table 1.

Compounds are abbreviated as follow hereinafter.
TEMPO: 2,2,6,6-tetramethylpiperidinooxyl
4H-TEMPO: 4-hydroxy-2,2,6,6-tetramethylpiperidinooxyl
TRIS-TEMPO: 4,4',4''-tris-(2,2,6,6-tetramethylpiperidinooxyl)sulfide
HQ: hydroquinone
PTZ: phenothiazine

| Run No. | Inhibitors (ppm by weight) | | | Induction period (min) |
|---|---|---|---|---|
| | N-oxyl compd. | HQ | PTZ | |
| 1 | 4H-TEMPO 1 | 0 | 0 | 8 |
| 2 | — | 13 | 0 | 3 |
| 3 | — | 0 | 13 | 20 |
| 4 | 4H-TEMPO 1 | 13 | 0 | 10 |
| 5 | 4H-TEMPO 1 | 0 | 13 | 25 |
| 6 | — | 13 | 13 | 21 |
| 7 | 4H-TEMPO 1 | 6.5 | 6.5 | 38 |
| 8 | 4H-TEMPO 0.5 | 3.3 | 3.3 | 41 |
| 9 | TEMPO 1 | 6.5 | 6.5 | 40 |
| 10 | TRIS-TEMPO 1 | 6.5 | 6.5 | 35 |

From Table 1 it is clear that the inhibiting effect (expressed in terms of induction period) is better in experiments Nos. 7–10 (pertaining to the present invention) than in experiments Nos. 1–6 (for comparison) in which the inhibitors were used alone or in pairs. It is to be noted that experiment No. 8 gave a better result than experiments Nos. 4–6 although the total amount of the inhibitors is less. This suggests the importance of using the three inhibitors together.

Example 2

The inhibiting effect was evaluated in azeotropic separation of acrylic acid from its aqueous solution (containing 30 wt % water and 2.5 wt % acetic acid) resulting from the catalytic gas phase reaction of propylene. The azeotropic separation was carried out using a packed column with a feed pipe in the middle and a condenser at the top and also using methyl isobutyl ketone as reflux, with the pressure being 160 mmHg and the temperature being 49° C. at the top and 97° C. at the bottom. Each of the inhibitors shown in Table 2 was added to the reflux (which was fed to the column) and oxygen gas was fed to the bottom of the column. The amounts of the inhibitors and oxygen are based on the amount of evaporated acrylic acid. It was found that the bottom product in the steady state was comprised of 97 wt % acrylic acid and 0.5 wt % acetic acid, with the remainder being 2.5 wt %. After continued operation for 8 hours, with the reflux being recycled as such, the amount of polymers formed in the column was determined through suction drying to obtain constant weight. The results are shown in Table 2

TABLE 2

| Run No. | Inhibitors (ppm) | | | Amount of oxygen (vol %) | Amount of polymers formed (g) |
|---|---|---|---|---|---|
| | 4H-TEMPO | HQ | PTZ | | |
| 11 | 3.8 | 0 | 0 | 0.21 | 9.0 |
| 12 | 1 | 6.7 | 0 | 0.21 | 2.9 |
| 13 | 0.5 | 3.3 | 0 | 0.21 | 33.2 |
| 14 | 1 | 0 | 6.7 | 0.21 | 3.0 |
| 15 | 0.5 | 0 | 3.3 | 0.21 | 25.3 |
| 16 | 1 | 3.3 | 3.3 | 0.21 | 0.6 |

TABLE 2-continued

| Run | Inhibitors (ppm) | | | Amount of oxygen (vol %) | Amount of polymers formed (g) |
| --- | --- | --- | --- | --- | --- |
| No. | 4H-TEMPO | HQ | PTZ | | |
| 17 | 0.5 | 1.7 | 1.7 | 0.21 | 1.2 |

From Table 2 it is clear that the amount of polymers formed was less in experiments Nos. 16 and 17 (pertaining to present invention) than in experiments Nos. 11 to 15 (for comparison) in which the three inhibitors were not used together.

Example 3

Pure methacrylic acid was prepared from commercial one by distillation to remove inhibitors. 2 ml each of the pure methacrylic acid (placed in a test tube) was incorporated with inhibitors in different amounts as shown in Table 3. (Experiments Nos. 18 and 19 are for comparison.) The test tube was kept reducing pressure and immersed in an oil bath at 130° C.

Induction period of polymerization was measured by visual inspection. The results are shown in Table 3.

TABLE 3

| Run No. | Inhibitors (ppm) | | | Induction period (min) |
| --- | --- | --- | --- | --- |
| | 4H-TEMPO | HQ | PTZ | |
| 18 | 1 | 13 | 0 | 20 |
| 19 | 1 | 0 | 13 | 27 |
| 20 | 1 | 6.5 | 6.5 | 45 |
| 21 | 0.5 | 3.3 | 3.3 | 38 |

From Table 3 it is clear that the inhibiting effect (expressed in terms of induction period) is better in experiments Nos. 20 and 21 (pertaining to the present invention) than in experiments Nos. 18 and 19 (for comparison) in which the inhibitors were used in pairs. It is to be noted that experiment No. 21 gave a better result than experiments Nos. 18 and 19 although the total amount of the inhibitors is less.

Example 4

Four pure acrylate (methyl acrylate (AM), ethyl acrylate (AE), butyl acrylate (AB), and octyl acrylate (AO)) were prepared from commercial ones by distillation to remove inhibitors. 30 ml each of the pure acrylate (placed in a test tube) was incorporated with inhibitors in different amounts as shown in Table 4. The test tube was kept reducing pressure and immersed in an oil bath at 70° C. for AM, 90° C. for AE, and 120° C. for AB and AO. Induction period of polymerization was measured by heat generation. The results are shown in Table 4.

TABLE 4

| Run No. | Inhibitors (ppm) | | | Induction period (h) | | | |
| --- | --- | --- | --- | --- | --- | --- | --- |
| | 4H-TEMPO | HQ | PTZ | AM | AE | AB | AO |
| 22 | 1 | 13 | 0 | 11.0 | 10.5 | 7.5 | 20.5 |
| 23 | 1 | 0 | 13 | 77.5 | 79.0 | 57.0 | 139 |
| 24 | 1 | 6.5 | 6.5 | 141 | 135 | 89.5 | 233 |
| 25 | 0.5 | 3.3 | 3.3 | 106 | 117 | 68.0 | 178 |

From Table 4 it is clear that the induction period of all acrylates in experiments Nos. 24 and 25 (pertaining to the present invention) is longer than in experiments Nos. 22 and 23 (for comparison) in which the inhibitors were used in pairs.

Example 5

Two pure methacrylates (methyl methacrylate (MMA) and butyl methacrylate (BMA)) were prepared from commercial ones by distillation to remove inhibitors. 30 ml each of the pure methacrylates (placed in a test tube) was incorporated with inhibitors in different amounts as shown in Table 5. The test tube was kept reducing pressure and immersed in an oil bath at 90° C. for MMA and 120° C. for BMA.

Induction period of polymerization was measured in the same manner as in Example 4. The results are shown in Table 5.

TABLE 5

| Run No. | Inhibitors (ppm) | | | Induction period (h) | |
| --- | --- | --- | --- | --- | --- |
| | 4H-TEMPO | HQ | PTZ | MMA | BMA |
| 26 | 1 | 13 | 0 | 33.5 | 15.0 |
| 27 | 1 | 0 | 13 | 16.0 | 9.5 |
| 28 | 1 | 6.5 | 6.5 | 65.0 | 29.5 |
| 29 | 0.5 | 3.3 | 3.3 | 43.0 | 21.0 |

From Table 5 it is clear that the induction period in experiments Nos. 28 and 29 (pertaining to the present invention) is longer than in experiments Nos. 26 and 27 (for comparison) in which the inhibitors were used in pairs.

Example 6

Four pure (meth)acrylates (listed below) were prepared from commercial ones by distillation to remove inhibitors. 30 ml each of the pure (meth)acrylates (placed in a test tube) was incorporated with inhibitors in different amounts as shown in Table 5. The test tube was kept reducing pressure and immersed in an oil bath at 100° C.

Induction period of polymerization was measured by heat generation. The results are shown in Table 6.
HEA: 2-hydroxyethyl acrylate
HPA: 2-hydroxypropyl acrylate
HEMA: 2-hydroxyethyl methacrylate
HPMA: 2-hydroxypropyl methacrylate

TABLE 6

| Run No. | Inhibitors (ppm) | | | Induction period (h) | | | |
| --- | --- | --- | --- | --- | --- | --- | --- |
| | 4-H TEMPO | HQ | PTZ | HEA | HPA | HEMA | HPMA |
| 30 | 1 | 13 | 0 | 29.5 | 91.0 | 72.0 | 37.5 |
| 31 | 1 | 0 | 13 | 35.0 | 100.0 | 84.5 | 45.5 |
| 32 | 1 | 6.5 | 6.5 | 57.0 | 175.0 | 145.0 | 71.0 |
| 33 | 0.5 | 3.3 | 3.3 | 49.5 | 133.5 | 113.5 | 59.5 |

From Table 6 it is clear that the inhibiting effect in experiments Nos. 32 and 33 (pertaining to the present invention) is better than in experiments Nos. 30 and 31 (for comparison).

Example 7

The inhibiting effect was evaluated in azeotropic separation of acrylic acid from its aqueous solution (containing 30 wt % water and 2.5 wt % acetic acid) resulting from the catalytic gas phase reaction of propylene. The azeotropic separation was carried out using a distillation column (105 mm in inside diameter) equipped with 50 stainless steel sieve trays at intervals of 147 mm, with a feed pipe in the middle and a condenser at the top and also using methyl isobutyl ketone as reflux, under the following conditions.

Temperature at the column top: 46° C.
Temperature at the column bottom: 97° C.
Pressure at the column top: 110 mmHg
Pressure at the column bottom: 152 mmHg
Amount of feed at the 37th tray: 10.58 L/h
Amount of reflux: 19.54 L/h
Amount of discharge from the bottom: 7.05 L/h
Amount of water phase distilled: 3.94 L/h
Amount of oil phase distilled: 19.74 L/h
R/D=0.92 (in molar ratio)

Each of the following inhibitors was added to methyl isobutyl ketone (which was fed to the top of the column) and oxygen gas was fed to the bottom of the column in an amount of 0.3 vol %.

4-hydroxyl-2,2,6,6-tetramethylpiperidinooxyl (4H-TEMPO), 30 ppm hydroquinone (HQ), 100 ppm phenothiazine (PTZ), 100 ppm The amounts of the inhibitors and oxygen are based on the amount of evaporated acrylic acid.

It was found that the bottom product in the steady state was comprised of 97.2 wt % acrylic acid and 0.5 wt % acetic acid, with the remainder being 2.3 wt %, the water phase distilled was composed of 90.8 wt % water, 0.4 wt % acrylic acid, 6.5 wt % acetic acid, and 2.3 wt % methyl isobutyl ketone, and the oil phase distilled was composed of 86.7 wt % methyl isobutyl ketone, 3.9 wt % water, 1.4 wt % acrylic acid, 6.5 wt % acetic acid, with the remainder being 1.5 wt %. The oil phase distilled was recycled as the reflux. The inhibiting effect was evaluated by observing the pressure drop in the column or flooding or by disassembling the column. It was possible to carry out continued operation for 14 days in a stable manner. The distillation column was disassembled for inspection after the stop of operation. The formation of polymers was not found at all.

Comparative Example 1

The same procedure as in Example 7 was repeated except that PTZ was omitted and the amount of HQ was increased to 200 ppm (with the total amount of the inhibitors remaining unchanged). After 2 days, it became impossible to continue operation due to pressure drop in the column. Inspection by disassembling the column revealed the formation of popcorn polymers. The result indicates that the two inhibitors alone (N-oxyl compound and phenol compound) are not enough to provide the desired inhibiting effect.

Comparative Example 2

The same procedure as in Example 7 was repeated except that HQ was omitted and the amount of PTZ was increased to 200 ppm (with the total amount of the inhibitors remaining unchanged). After 4 days, it became impossible to continue operation due to pressure drop in the column. Inspection by disassembling the column revealed that formation of popcorn polymers. The result indicates that the two inhibitors alone (N-oxyl compound and phenothiazine) are not enough to provide the desired inhibiting effect.

What is claimed is:

1. A method for inhibiting the polymerization of (meth)acrylic acid and esters thereof, said method comprising using as the inhibitor N-oxyl compound, phenol compound, and phenothiazine compound in combination with one another.

2. A method for inhibiting polymerization as defined in claim 1, wherein the inhibitor is used in total amount of 10-1000 ppm (by weight) of the amount of evaporated (meth)acrylic acid or esters thereof.

3. A method for inhibiting polymerization as defined in claim 1, wherein the N-oxyl compound, phenol compound, and phenothiazine compound are used in an amount of 1-100 ppm, 3-500 ppm, and 3-500 ppm (by weight), respectively, of the amount of evaporated (meth)acrylic acid or esters thereof.

4. A method for inhibiting polymerization as defined in any of claims 1 to 3, wherein the N-oxyl compound is one or more kinds selected from 2,2,6,6-tetramethylpiperidinooxyl, 4-hydroxy-2,2,6,6-tetramethylpiperidinooxyl, and 4,4',4''-tris(2,2,6,6-tetramethylpiperidinooxyl)phosphite.

5. A method for inhibiting polymerization as defined in any of claims 1 to 3, wherein the phenol compound is hydroquinone and/or methoquinone.

6. A method for inhibiting polymerization as defined in any of claims 1 to 3, wherein the phenothiazine compound is phenothiazine.

7. A method for inhibiting polymerization as defined in any of claims 1 to 3, wherein the N-oxyl compound is one or more kinds selected from 2,2,6,6-tetramethylpiperidinooxyl, 4-hydroxy-2,2,6,6-tetramethylpiperidinooxyl, and 4,4',4''-tris(2,2,6,6-tetramethylpiperidinooxyl)phosphite, the phenol compound is hydroquinone and/or methoquinone, and the phenothiazine compound is phenothiazine.

* * * * *